United States Patent [19]

Kabra et al.

[11] Patent Number: 6,027,795
[45] Date of Patent: Feb. 22, 2000

[54] SUPERABSORBENT FOAMS AND METHOD FOR PRODUCING THE SAME

[75] Inventors: Bhagwati G. Kabra, Ft. Worth, Tex.; Stevin H. Gehrke, Cincinnati, Ohio

[73] Assignee: University of Cincinnati, Cincinnati, Ohio

[21] Appl. No.: 08/823,897

[22] Filed: Mar. 17, 1997

Related U.S. Application Data

[60] Continuation of application No. 08/458,106, Jun. 1, 1995, abandoned, which is a division of application No. 08/242,548, May 13, 1994, Pat. No. 5,573,994.

[51] Int. Cl.$^7$ .................................. B32B 3/26; C08J 9/28
[52] U.S. Cl. ..................................... 428/305.5; 428/315.7; 428/321.1; 502/402; 502/404; 521/63; 521/64; 521/905
[58] Field of Search .............................. 428/305.5, 315.7, 428/321.1, 322.7; 502/402, 404, 439, 514; 521/902, 62, 63, 64

[56] References Cited

U.S. PATENT DOCUMENTS

| | | | |
|---|---|---|---|
| 4,444,922 | 4/1984 | Gutowski et al. | 523/338 |
| 5,338,766 | 8/1994 | Phan et al. | 521/63 |
| 5,484,818 | 1/1996 | De Vos et al. | 521/123 |

FOREIGN PATENT DOCUMENTS

| | | |
|---|---|---|
| 0 060 138 | 9/1982 | European Pat. Off. . |

OTHER PUBLICATIONS

Controlling the swelling characteristics of temperature–sensitive cellulose ether hydrogels, Harsh et al., Journal of Controlled Release, 17, pp. 175–185, 1991.

Low–density, microcellular polystyrene foams, Aubert et al., Polymer, vol. 26, pp. 2047–2054, 1985.

Preparation of multishell ICF target plastic foam cushion materials by thernally induced phase inversion processes, Young et al., J. Vac. Sci. Technol., 20(4); pp. 1094–1097, Apr. 1982.

Analysis Of Kinetic Behavior Of Temperature–Sensitive Water–Absorbing Hydrogel, X. Huang et al., Journal of Chemical Engineering of Japan, vol. 20, No. 2, pp. 123–128 (1987).

Controlling Swelling Characteristics of Novel Cellulose Ether Hydrogels, D.C. Harsh, et al., Abstract of Presentation, published by American Chemical Society Cellulose Division (1992).

Cross–Linked Polystyrene Incorporating Water Pools, F. M. Menger and T. Tsuno, J. Am. Chem. Soc., 112, pp. 1263–1264 (1990).

Design and synthesis of macroporous polymeric separation media based on substituted phenols, W. Rolls et al., Polymer, vol. 31, pp. 165–169 (1990).

Effect of several dual solvents on the phase separation of poly(4–methyl–1–pentene), J. M. Williams an J. E. Moore, Polymer, vol. 30, pp. 2279–2283 (1989).

High–density foams prepared with the styrene–divinylbenzene copolymer/heptane system, J. M. Williams and M. H. Wilkerson, Polymer, vol. 31, pp. 2162–2170 (1990).

Macroporous Polymers Derived From Vinylamine; Synthesis And Characterization, H. Tbal, et al., Eur. Polym., J., vol. 25, No. 4, pp. 331–340 (1989).

Rate–Limiting Steps for Sorption By Microporous Stimuli–Sensitive Absorbent Gels, B.G. Kabra and S.H. Gehrke, ACS Polymeric Materials Science & Engineering, vol. 69, pp. 533–534, Aug. 1993.

Spatial Distribution of the Phases in Water–in–Oil Emulsions, Open and Closed Microcellular Foams from Cross–Linked Polystyrene, J. M. Williams and D. A. Wrobleski, Langmuir, 4, pp. 656–662 (1988).

Structural Aspects of Porous Gels, Makromol. Chem. Macromol. Symp. 22, 253–268 (1988).

Synthesis and Characterization of Fast Response Absorbent Gels, B. Kabra and S.H. Gehrke, Abstract of Presentation, published by American Institute of Chemical Engineers (1991).

Synthesis of fast response, temperature–sensitive poly (N–isopropylacrylamide) gel, B.G. Kabra and S.H. Gehrke, Polymer Communications, vol. 32, No. 11, pp. 322–323 (1991).

Volume change kinetics of temperature–sensitive poly (vinyl methyl ether) gel, B.G. Kabra, et al., Polymer, vol. 33, No. 5, pp. 990–995 (1992).

Thermo–Responsive Polymer Gel, O. Hirasa, Nippon Gomu Kyokaishi, vol. 63, No. 1, pp. 29–39 Jan. 1990.

Preparation and Mechanical Properties of Thermo–Responsive Fibrous Hydrogels Made From Poly(vinyl methyl ether)s, O. Hirasa, et al., Konbunshi Robunshu, vol. 46, No. 11, pp. 661–665 (1989).

Thermo–responsive Polymer Hydrogel, H. Hirasa, Research Institute for Polymers and Textiles (no date).

Primary Examiner—Blaine Copenheaver
Attorney, Agent, or Firm—Frost & Jacobs LLP

[57] ABSTRACT

An absorbent, microporous foam comprising a crosslinked polymer having interconnected fluid cells distributed throughout its mass, wherein the fluid cells have a diameter of between about 0.1 and about 100 $\mu$m, and wherein the foam can rapidly absorb at least about twice its dry weight in fluid, is disclosed. Also disclosed is a method for producing such microporous, absorbent foams. In this method: (a) a crosslinkable polymer and a first solvent are mixed to form a stable solution which can be induced to phase separate; (b) the stable solution is induced to phase separate into a polymer concentrated phase and a polymer dilute phase; (c) the polymer is induced to crosslink in the polymer concentrated phase for a predetermined period of time thereby forming a microporous material; and (d) the microporous material is dried to produce the absorbent foam.

6 Claims, No Drawings

SUPERABSORBENT FOAMS AND METHOD FOR PRODUCING THE SAME

This is a continuation of application Ser. No. 08/458,106, filed Jun. 1, 1995, now abandoned, which is a divisional of application Ser. No. 08/242,548, filed May 13,1994, now U.S. Pat. No. 5,573,994.

BACKGROUND OF THE INVENTION

1. Field of the Invention

This invention relates to microcellular, open-celled, superabsorbent polymer foams, and a method for producing the same. The foams thus produced have exceptionally rapid sorption rates, as they absorb and retain liquid by a combination of capillary action and pore wall swelling.

2. Description of Related Art

Microporous, open-celled foams have garnered much interest recently due to their potential for numerous and varied applications. For example, these materials are useful in multishell fusion target experiments, as filtration media, in controlled release systems, and as artificial skin and blood vessels. Microporous, open-celled foams can also be employed in much simpler consumer applications such as reusable diapers and other personal hygiene devices. These latter uses often depend upon the absorbent capabilities of the foam and rate of sorption, as well as its strength.

Foams can generally be characterized as materials which have numerous fluid-filled cells distributed throughout their mass. The properties of these materials vary greatly, and depend in large part on the degree of interconnectivity of the cells. For example, should it be desired to use the foam as an absorbent, a greater degree of interconnectivity is desired. If the cells in this two phase fluid-solid system are interconnected, the material is termed an "open-celled" foam. Ideally, a foam used for absorbent purposes should have 100% interconnectivity, in which case the material is termed "bicontinuous" or "open-celled." In contrast, closed cell foams have cells which are discrete, having fluid phases which are independent of that of the other cells.

Another characteristic which greatly affects the properties of a foam is the size of its pores. For example, while natural sponge is a well-known absorbent, it cannot be used in products such as diapers because its large, macroscopic pores cannot hold fluids under even the slightest pressure. For a foam to be useful in a diaper, fluid must be retained under a pressure of about 0.5 psi. In order to achieve this level of retention, the pores must be microscopic, since only then will the capillary forces responsible for fluid retention be sufficient to withstand applied pressures at the desired levels. In addition, only microscopic pores will retain fluid in competition with other absorbent materials such as clothing ("wicking"). Thus, microporous foams (0.1–100 $\mu$m pores) are desired for absorbent purposes.

Conventional, macroporous (>100 $\mu$m pores) polymeric foams can be produced by a number of methods, the most common being a gas dispersion process whereby a gaseous phase is dispersed throughout a liquid polymer phase. The resultant gas-solid state is then preserved either by physical means such as vitrification, or by polymerization and/or crosslinking of the liquid phase. The cell size in these foams, however, is generally 100–200 $\mu$m or larger, and thus their usefulness as absorbents is limited. These products do find use as insulation and packaging material.

Microporous (i.e., 0.1–100 $\mu$m pores) polymeric foams have generally been produced by phase separation techniques, however these methods are generally only suitable for hydrophobic polymers. For example, polystyrene foams having densities of 0.02 to 0.20 g/cm$^3$ and cell sizes of 1–20 $\mu$m have been produced. Typically, a homogeneous polymer/solvent solution is first prepared. This solution is then permitted to phase separate by either dissolving a nonsolvent for the polymer in the solution, decreasing the temperature to a point below the upper consolute solution temperature (UCST), or both. Most non-aqueous polymer/solvent systems capable of phase separating exhibit an UCST, and these polymers are typically hydrophobic. After phase separation, the temperature is further reduced to either below the freezing point of the solvent or below the glass transition temperature in order to lock in the desired structure. The solvent can then be removed from the porous, polymer structure either by freeze drying or supercritical drying to produce a microcellular foam. Unfortunately, simple evaporation of the solvent may not be employed for these products because large capillary forces at the liquid-vapor interface will cause the structure to shrink or crack, resulting in the destruction of the cells. In addition, although the expensive and tedious procedures of freeze-drying or supercritical drying may be employed, the resulting microporous foam will redissolve when brought into contact with a good solvent and melt when subjected to elevated temperatures.

Thus, there is a need for microcellular, open-celled foams which exhibit superabsorbency and can be readily synthesized from numerous polymer/solvent systems, particularly hydrophilic polymers.

SUMMARY OF THE INVENTION

While not exclusive, the following describes some of the important features and objects of the present invention.

It is an object of the present invention to provide a method for producing microporous, open-celled foam.

It is another object of the present invention to provide a method for producing microporous, open-celled foam which can be employed with numerous types of polymer/solvent systems.

It is yet another object of the present invention to provide microporous, open-celled foams, as well as a method for producing the same, wherein these foams which exhibit superabsorbancy, can be dried by a number of different methods, and which retain a significant amount of liquid even under pressure. These foams will absorb and retain liquid by a combination of capillary action and pore wall swelling.

It is still another object of the present invention to provide a method for producing microporous, open-celled foam, wherein the properties of the foam can be regulated by the choice of synthesis parameters.

The foregoing objects can be accomplished by providing a method for producing a microporous, open-celled foam, comprising the steps of: (a) mixing a cross-linkable polymer and a first solvent to form a stable solution, preferably a substantially homogeneous, single-phase solution, wherein the stable solution can be induced to phase separate (preferably upon a change in temperature of the solution); (b) inducing the stable solution to phase separate into a polymer-concentrated phase and a polymer-dilute phase after a predetermined period of time; (c) inducing crosslinking of said polymer, so that the polymer will crosslink in said concentrated phase for a predetermined period of time during the phase separation to thereby form a microporous material; and (d) drying the microporous material to produce the absorbent foam. Preferably, crosslinking is induced prior to the phase separation, and is permitted to continue for a predetermined period of time prior to phase separation. Optionally, the solution may be returned to a single phase condition, and further crosslinked in this state to produce the desired foam. The single-phase solution may exhibit a lower consolute solution temperature or an upper consolute solution temperature, and phase separation is preferably induced by increasing or decreasing the temperature of the single-phase solution to a point above or below the lower consolute solution temperature or the upper consolute solution temperature, respectively. If necessary, a phase-separation enhancer may be added to the single-phase solution prior to inducing phase separation so as to assist the stable solution to phase-separate, either in conjunction with a temperature change or at a constant temperature. Suitable phase separation enhancers include other solutes such as a salt, other solvents, or even additional polymer. The foams may be dried by a number of different methods, and it is preferred that any uncrosslinked sol fraction be removed from the foam prior to drying.

Drying of the microporous materials produced by the methods of the present invention to produce the desired foams may be accomplished by air-drying, freeze-drying, or a solvent-exchange method. This latter method of drying is accomplished by placing the material in a second solvent, thereby replacing any of the synthesis (or "first") solvent which is present in the material with the second solvent. The microporous material may then be air-dried to evaporate the second solvent, or the solvent-exchange method repeated using a third solvent. It is preferable that if second and third solvents are employed that the second solvent be miscible with the synthesis solvent, and that the third solvent be miscible with the second solvent and a non-solvent for the polymer itself. In this fashion the third solvent will not be absorbed by the cell walls, and the evaporation process will not exert as great a force on the pores. It is also preferably that the second and third solvents (if employed) exhibit a high degree of volatility.

The synthesis method of the present invention may be employed with any polymer/solvent system which can be induced to phase separate, and wherein the polymer is crosslinkable. The polymer, for example, may be chosen from the following:

hydrophobically modified carbohydrate polymers, including: hydroxypropyl dextran, hydroxypropyl guar, hydroxypropyl starch, hydroxypropyl cellulose (HPC), hydroxyethyl cellulose (HEC), methyl cellulose, hydroxypropylmethyl cellulose, and ethylhydroxyethyl cellulose poly(vinyl alcohol-co-vinyl acetate)

poly(methacrylic acid)

cyanoethylated or partially formalized poly(vinyl alcohol)

poly-N-vinyl-2-oxazolidone polypeptides, including: poly(L-proline), and poly(valine-proline-glycine-X-glycine), wherein X=any amino acid acrylate (or analogous methacrylate) copolymers, including: hydroxypropyl acrylate-co-acrylamide, diacetone acrylamide-co-hydroxyethyl acrylate, and hydroxypropyl acrylate-co-hydroxyethyl acrylate N-alkylacrylamide (or analogous N-alkylmethacrylamide) derivatives including: ethylacrylamide, cyclopropylacrylamide, n-propylacrylamide, and isopropylacrylamide.

The polymer is preferably HEC.

The crosslinker may be chosen from the following: acetaldehyde, formaldehyde, glutaraldehyde, diglycidyl ether, divinyl sulfone, diisocyanates, dimethyl urea, epichlorohydrin, oxalic acid, phosphoryl chloride, trimetaphosphate, trimethylomelamine, polyacrolein, and ceric ion redox systems Preferably, the crosslinker is divinyl sulfone, when the polymer is either HPC or HEC.

There is also provided a method for producing a microporous, open-celled foam, comprising the steps of: (a) mixing hydroxypropyl cellulose (HPC) and water to form a substantially homogeneous, single-phase solution; (b) inducing crosslinking of the HPC by adding a suitable crosslinking agent to the single-phase solution; (c) inducing phase separation of the single-phase solution into a polymer-concentrated phase and a polymer-dilute phase after a predetermined period of time, wherein phase separation is induced by increasing the temperature of the single-phase solution to above the lower consolute solution temperature of the single-phase solution; and (d) permitting crosslinking to continue in the concentrated phase after inducing phase separation to thereby form an open-celled foam. The crosslinker is preferably divinyl sulfone (DVS). The concentration of HPC may be between about 1.9 and about 25 weight percent of the total weight of the single-phase solution, and is preferably about 4 weight percent. The pH of the single-phase solution should preferably be above about 11, and more preferably about 12. The molecular weight of the HPC employed is between about 100,000 and about 1,000,000, preferably about 400,000. The concentration of DVS is preferably between about 0.2 and about 5.5 weight percent of the single phase solution, and more preferably about 2 weight percent. Phase separation of these aqueous polymer solution can be induced by increasing the temperature of the solution to above about 40° C., preferably to a temperature of about 50° C. Phase separation may be induced after the crosslinking has proceeded for between about 1 and about 45 minutes (preferably about 5 minutes), and the crosslinking may be permitted to continue after inducing phase separation for between about 0.3 and about 100 hours (preferably about 24 hours). Excessive incubation at a high temperature and pH should be avoided, as it may cause polymer degradation.

A method for producing a microporous, open-celled foam, is provided, wherein this method comprises the steps of: (a) mixing hydroxyethyl cellulose (HEC), water and a phase-separation enhancer to form a substantially homogeneous, single-phase solution, wherein the phase-separation enhancer is chosen from the group consisting of: a salt, a water-soluble organic solvent, and a combination of a salt and a water-soluble organic solvent; (b) inducing crosslinking of the HEC by adding a suitable crosslinking agent to the single-phase solution; (c) inducing phase separation of the single-phase solution into a polymer-concentrated phase and a polymer-dilute phase after a predetermined period of time, wherein phase separation is induced by increasing the temperature of the single-phase solution to a point above the lower consolute solution temperature of the single-phase solution; and (d) permitting crosslinking to continue in the concentrated phase after phase separation is induced to thereby form an open-celled foam. The crosslinking agent is preferably divinyl sulfone (DVS), and the phase separation enhancer is preferably sodium chloride. Phase separation may be induced by increasing the temperature of the solution to above about 94° C., preferably to about 95° C. The pH of the single-phase solution is preferably above about 11, and more preferably about 12. The concentration of HEC is preferably between about 1.3 and about 8 weight percent of the total weight of the single-phase solution and the DVS, more preferably about 3 weight percent. The concentration of DVS is preferably between about 0.4 and about 2 weight percent, and more preferably about 1.6 weight percent. Phase separation may be induced after crosslinking has proceeded for between about 1 and about 3 minutes, preferably about 2.5 minutes. Crosslinking may then be permitted to continue, after phase separation is induced, for between about 20 and about 240 minutes, and preferably for about 60 minutes.

The HPC and HEC foams produced by the methods described above may also be dried by the three methods previously described. If the solvent-exchange method is employed, these foams may be dried using any of a number of second solvents including: methanol, ethanol, 1-propanol, 2-propanol, 1-butanol, sec-butanol, and acetone. If both a second and third solvent are employed in the drying process, the third solvent may, for example, be pentane, hexane or heptane. HPC and HEC foams are preferably dried by the solvent-exchange process using an ethanol-pentane solvent system. Other solvents in addition to those specifically enumerated may also be employed, and the choice of solvent(s) do not appreciably affect the foam properties. It is preferred, however, that the final solvent employed prior to drying be a non-solvent for the polymer.

There is also provided an absorbent (preferably superabsorbent), microporous foam comprising a crosslinked polymer having interconnected fluid cells distributed throughout its mass, wherein the fluid cells have a diameter of between about 0.1 and about 100 $\mu$m, and wherein the foam can rapidly absorb at least about twice its dry weight in fluid. These foams preferably absorb and retain fluid by a combination of capillary action and pore wall swelling. The foams also do not lose a significant amount of resorption capacity upon repeated swellin/drying cycles, and the polymers employed are preferably hydrophilic. The polymers employed also preferably exhibit a lower consolute solution temperature (LCST) in an aqueous solution and phase separate from an aqueous solution as the temperature of the solution is increased to above said LCST. The polymer employed is preferably HPC or HEC.

DESCRIPTION OF THE PREFERRED EMBODIMENT

Applicants have discovered a method for producing microcellular, open-celled foams, which preferably exhibit superabsorbency. As used herein, an absorbent foam is one which absorbs at least twice its dry weight in fluid, and a superabsorbent foam is one which absorbs at least ten times its dry weight in fluid. Additionally, the resulting foams will swell, rather than dissolve, when placed in good solvents. The foams can be produced in any size or shape, and the method is readily applicable to numerous polymer/solvent systems which exhibit certain characteristics. The superabsorbent foams produced by the method of the present invention can be employed in any application wherein the foams of the prior art are used. In addition, the foams of the present invention can also be employed in biomedical applications (e.g., artificial blood vessels, tissue supports, implants, artificial skin, and controlled release drug delivery systems), packing for chromatography columns, reusable diapers, personal hygiene products such as tampons, and generally as a substitute for conventional superabsorbents. These foams can also be produced from hydrophilic polymers, thereby providing a product which is particularly suitable for biomedical applications since such products generally display good biocompatibility. Such hydrophilic foams will absorb and retain water by a combination of capillary action and swelling of the pore walls. The porosity and pore size of the foams can also be precisely controlled by varying the synthesis parameters.

Many homogeneous polymer/solvent solutions can be induced to phase separate into polymer-concentrated and polymer-dilute phases merely by a change in temperature. After the polymer is dissolved in a solvent, phase separation can usually be induced by increasing the temperature to a point above the lower consolute solution temperature (LCST). Some polymer/solvent systems (particularly non-aqueous solvents) exhibit an upper consolute solution temperature (UCST), and thus in these systems phase separation is induced by decreasing the temperature to a point below the UCST. In addition, the LCST or UCST can be modified when needed by the addition of other solutes or solvents ("phase separation enhancer").

During the early stages of phase separation an interconnected morphology exists, and the applicants have found that open-celled, superabsorbent foams can be produced if this interconnected morphology can be preserved in the final product. Phase separation can also be induced by a number of other means while still producing the interconnected or bicontinuous structure during the phase separation. Typically, this interconnected structure is achieved merely by moving the polymer/solvent solution from a thermodynamically stable phase to a thermodynamically unstable condition. One skilled in the art can quite readily accomplish the phase separation merely by employing the polymer/solvent phase diagram for the particular polymer/solvent system employed. In addition to inducing phase separation by raising or lowering the temperature, the addition of a phase separation enhancer (with or without a change in temperature) may also induce phase separation. Suitable phase separation enhancers include: solutes such as salts, other solvents, additional polymer of the type used in the synthesis. If a solvent phase separation enhancer employed is a non-solvent for the polymer but is miscible with the solvent of the homogeneous polymer/solvent system, phase separation can be induced by spreading the enhancer over the surface of the polymer/solvent solution to form sheets or by dispersing the polymer/solvent solution in the enhancer to form particles. The phase separation enhancer can even be merely mixed with the polymer/solvent solution in order to induce phase separation. The use of a phase separation enhancer may also be combined with a change in solution temperature in order to induce phase separation, particularly when the phase separation is additional polymer.

The initial thermodynamically-stable state may even be in the form of a suspension or emulsion. The suspension or emulsion can then be induced to phase separate into a thermodynamically unstable condition by any of the methods described above, thereby providing a polymer-concentrated and a polymer-dilute phase.

In general, the foams of the present invention can be prepared from any polymer having reactive functional groups (i.e., can be crosslinked). The polymer is first solvated in order to form a stable, preferably homogeneous solution. The polymer is then preferably crosslinked in this stable solution for a predetermined period of time in order to form a limited crosslinked network, which can help provide a macroscopic structure for the final foam product. It should be noted, however, that crosslinking prior to phase separation may be omitted in some instances. The partially crosslinked, stable polymer solution is then induced to phase separate, usually by quickly changing the solution temperature, thereby resulting in interconnected polymer-concentrated and polymer-dilute phases. The polymer-concentrated phase is crosslinked into dense regions as the phase separation is occurring, thereby forming an open-celled network of crosslinked polymer with sol fraction occupying the cells. The crosslinked polymer-concentrated phase forms the cell walls, while the uncrosslinked, polymer-dilute phase is contained within the cells, thereby preserving the desired interconnected or bicontinuous structure. Complete phase separation cannot occur, however, because the crosslinking reaction freezes the desired microstructure. The extent of crosslinking in the phase-separated state can be varied, and the solution can even be returned to the homogenous state and the crosslinking continued if desired. The sol fraction is then removed, and the product dried, to produce the desired absorbent foam.

The process of the present invention can be performed using any polymer/solvent system which can be induced to phase separate, as long as the polymer is crosslinkable (i.e., has reactive functional groups). Typical functional groups which are easily reacted include hydroxyl, amine, carboxylic acid and amino, however the present invention is not limited to these examples. Polymers which may be employed in the method of the present invention include:

1. Hydrophobically modified carbohydrate polymers, including:
   hydroxypropyl dextran
   hydroxypropyl guar
   hydroxypropyl starch
   hydroxypropyl cellulose
   hydroxyethyl cellulose
   methyl cellulose
   hydroxypropylmethyl cellulose
   ethylhydroxyethyl cellulose
2. Poly(vinyl alcohol-co-vinyl acetate)
3. Poly(methacrylic acid)
4. cyanoethylated or partially formalized poly(vinyl alcohol)
5. Poly-N-vinyl-2-oxazolidone
6. Polypeptides, including:
   poly(L-proline)
   poly(valine-proline-glycine-X-glycine), wherein X=any amino acid
7. Acrylate (or analogous methacrylate) copolymers, including:
   hydroxypropyl acrylate-co-acrylamide
   diacetone acrylamide-co-hydroxyethyl acrylate
   hydroxypropyl acrylate-co-hydroxyethyl acrylate
8. N-alkylacrylamide (or analogous N-alkylmethacrylamide) derivatives, including:
   ethylacrylamide
   cyclopropylacrylamide
   n-propylacrylamide
   isopropylacrylamide All of the polymers listed above can be readily crosslinked, and exhibit LCST behavior in aqueous solutions. Thus, these polymers can be used to prepare superabsorbent, microporous foams which rapidly absorb fluid by a combination of capillary force and pore wall swelling.

Any crosslinker suitable for the particular polymer/solvent system employed can be used, particularly the types used to produce conventional superabsorbents from polymers such as starch (e.g., divinyl sulfone). These crosslinking agents are generally di- or multi-functional crosslinking agents which react with the pendant polymer functional groups. Suitable crosslinking agents include:

acetaldehyde
formaldehyde
glutaraldehyde
diglycidyl ether
divinyl sulfone
diisocyanates
dimethyl urea
epichlorohydrin
oxalic acid
phosphoryl chloride
trimetaphosphate
trimethylomelamine
polyacrolein
ceric ion redox systems Other known crosslinking means may be employed, including photo-crosslinking, as well as other "physical" crosslinking means. By physical crosslinking it is meant that the crosslinking occurs by non-covalent bonding, whereas chemical crosslinking (e.g., by the list of crosslinkers set forth above) results in the formation of new covalent bonds within the product. Physical crosslinking can occur due to non-covalent hydrophobic interactions between hydrophobic polymer side chains of a polymer. This effect can often be enhanced by the addition of a surfactant, and the term crosslinker in the context of the present application is considered to include such surfactants (a physical crosslinking agent). One such polymer which can be crosslinked in this manner is hydrophobically modified hydroxyethyl cellulose (HMHEC) (available from Aqualon Co., Wilmington, Del., as Natrosol Plus®). Other types of physical crosslinking include hydrogen-bonding, van der Waals interactions, ionic bonding, hydrogen bonding, coordination interactions, and salt bridges. The present invention is considered to include crosslinking by any of these physical methods, and these types of crosslinking are set forth in further detail in *Absorbent Polymer Technology*, edited by L. Brannon-Peppas and R. S. Harland, Elsevier Science Publishing Co. Inc., New York (1990).

After the product has been permitted to phase separate while crosslinking for a predetermined period of time (a time sufficient to provide strength to the final foam product), the product must be dried in order to produce a microporous material suitable for use as an absorbent foam. The sol fraction may be removed from the product by any of a number of means, but preferably merely by leaching the sol from the microporous material using the same solvent employed in the synthesis reaction (e.g., water). The product may then be air-dried at room temperature, or even in a conventional or microwave oven, in order to evaporate the solvent and produce a foam. Freeze-drying (any conventional means) or solvent-exchange may also be utilized.

The properties of the foams produced by the methods of the present invention can be readily tailored to one's needs, and one skilled in the art would be able to readily prepare suitable foams from any polymer/solvent system wherein said system can be induced to phase separate and wherein said polymer is crosslinkable. Polymer/solvent phase diagrams are readily available in the literature, or can be easily prepared in the laboratory. Suitable crosslinkers for polymers are also well-known, and thus one skilled in the art could readily identify a crosslinker suitable for the polymer/solvent solution employed. For the preferred polymers which exhibit a LCST in aqueous solutions, selection criteria are set forth in the work by L. D. Taylor and L. D. Cerankowski, J. Polymer Science: Polymer Chemistry Edition, Vol. 13, pp. 2351–2570 (1975). In fact, the authors of this work stated that "the LCST phenomenon, rather than being a rare curiosity, is quite predictable and easy to achieve." Even polymers which are extremely hydrophilic (totally miscible in water at all temperatures) can be modified to the point that they exhibit LCST behavior. This can be accomplished, for example, by merely copolymerizing the precursor monomer with a more hydrophobic monomer (e.g., acrylamide with hydroxypropyl acrylate) to produce a crosslinkable polymer which exhibits the desired LCST behavior. It should be pointed out that, even though the copolymer exhibits LCST behavior, it is still relatively hydrophilic and therefore the resultant foam will absorb and retain water by a combination of capillary forces and pore wall swelling.

The properties of the superabsorbent foams will depend upon a number of factors, including: precursor polymer type, molecular weight of the polymer, initial polymer concentration, crosslinker concentration, pH of the polymer/solvent solution, reaction time prior to phase separation and reaction time during and after phase separation. By varying these parameters, the properties of the foams produced can be tailored to one's needs. The most significant properties of these foams include: porosity, sorption capacity, sorption rate, pore size, pore wall thickness, and compression strength. The synthesis parameters of the method of the present invention can be readily adjusted by one skilled in the art in order to produce a foam of the desired properties, particularly the desired rigidity. For example, increasing the initial polymer concentration will decrease the porosity of the foam while increasing the strength of the foam. Pore sizes can be reduced by increasing the amount of crosslinking which occurs prior to phase separation. Pore size (as well as pore wall thickness) will also decrease with corresponding increases in the initial polymer concentration, molecular weight of the polymer, or crosslinker concentration. Crosslinking during phase separation should, however, proceed for a time sufficient to ensure that the foam product will not collapse significantly under a modest load.

In general, the foams of the present invention are superabsorbent, and their improved properties over that of the prior art are due, in part, to the fact that these foams absorb and retain liquid not only by capillary action, but also by a swelling of the pore walls. Unlike prior art foams, foams can be produced by the method of the present invention which can be air-dried while still producing a foam with good structural properties.

EXAMPLE 1

Hydroxypropyl cellulose (HPC) (available from Aldrich Chemical Co.) was dissolved in an aqueous NaOH solution. An alkaline pH was maintained in order to catalyze the crosslinking reaction. This solution was then maintained in a glass vial at room temperature for at least 24 hours in order to ensure complete and uniform hydration of the polymer. A predetermined amount of divinyl sulfone (DVS) was then added, and the solution was mixed thoroughly for approximately 30 seconds.

The polymer/crosslinker solution was next poured onto a glass plate (6"×6"×0.12") between silicone rubber gaskets (1.6 mm thick), and then covered with a second glass plate. The plates were secured to one another using spring-loaded clamps, thereby forming a sealed mold containing the polymer/crosslinker solution. The crosslinking reaction was then permitted to proceed at room temperature for a predetermined period of time (reaction time before phase separation). The mold was next immersed in a constant temperature bath which was maintained above the LCST of the polymer/solvent solution. The polymer/solvent solution then began to phase separate, and the polymer-dense phase was crosslinked as the solution phase separated and thereafter.

After a predetermined period of time, the mold was removed from the bath and opened, and the sheet of microporous material was removed. The sheet was then soaked in water in order to leach out the sol fraction which contained small amounts of polymer and crosslinker which were not incorporated into the foam network. The sheets were next dried in air either at room temperature or at high temperature in an oven (either conventional or microwave) to produce the microporous foams. At room temperature the water-swollen sheets took approximately 10–20 hours to dry completely. Table 1 provides the synthesis parameters for the HPC foams produced according to this procedure.

The sheets can be air-dried more quickly by first replacing the water held within the water-swollen foam with a more volatile solvent such as heptane. Heptane, however, is immiscible in water, and thus the water-swollen sheets were first soaked in ethanol to replace the water. The ethanol-soaked sheets are then soaked in heptane, thereby replacing the ethanol with heptane. While the heptane will remove ethanol from the cell walls, it does not itself swell the pore walls because heptane is a non-solvent for HPC. Thus, the heptane-swollen sheets can be air-dried at room temperature in about 10 to 20 minutes. Various other solvent combinations may be employed as part of the drying process, and a single solvent drying method can certainly be employed also (i.e., drying directly after soaking the sheet in the second solvent). The solvent used in the drying process (the "second" solvent) should, however, be miscible with the solvent employed for the foam synthesis so that it will fully replace the synthesis solvent. If a third solvent is employed for the drying process (e.g., heptane), it should be miscible with the second solvent and a non-solvent for the polymer. In this manner, the pore walls will be free of solvent, and the foam will dry more quickly. One advantage of this solvent-exchange method is that the third solvent, since it does not swell the cell walls, will exert little pressure on the pores as it evaporates, thereby minimizing any loss of porosity caused by drying.

EXAMPLE 2

In order to examine foam properties and the effect of the various synthesis parameters of Table 1 on these properties, several tests were performed on the foams synthesized in Example 1. The porosity of the foam is defined as the ratio of the mass of water which can be mechanically squeezed from a water-swollen foam to the mass of the water-swollen foam (at 25° C.). This testing indicated that some water was retained within the pore walls, thereby swelling the polymer network itself, while water held within the micropores was forced out by the mechanical pressure.

The sorption capacity of the foam is defined as the ratio of the mass of the water-swollen foam to the mass of the dry foam (at 25° C.). In order to determine the effect of drying conditions on the ability of the foam to absorb water, the sorption capacity was determined both before and after the initial drying of the foam. The porosity and sorption capacity of the foams are shown in Table 2 below.

The results in Table 2 indicate that all of the foams absorbed many times their own weight in water, and a portion was retained in the pore walls even after the foams were mechanically compressed. One foam sample (F 22)

was even capable of absorbing more than 40 times its weight in water. In addition, drying the foams did not significantly affect their ability to reabsorb fluid. The data in Table 2 also indicates that the porosity of the foam generally increases with a decrease in the initial polymer concentration. Other trends are also apparent from the data shown above. Sample F19 did not expel any water under the application of mechanical force, and this was probably due to a lack of pore interconnectivity or small pore size. This is readily resolved, however, merely by, for example, reducing the reaction time prior to phase separation. Samples F01 and F27 were too fragile to characterize by Applicants' techniques.

TABLE 1

| Sample Number | Average Mol. Wt of Polymer | Initial Polymer Conc. (wt %) | Initial Crosslinker Conc. (wt %) | pH of Initial Solution | Phase Separation (°C.) | Rxn. Time Before Phase Separation (min) | Rxn. Time During Phase Separation (hr) |
|---|---|---|---|---|---|---|---|
| F 01 | 100,000 | 4.66 | 2.18 | 12.30 | 46.5 | 3.0 | 16.0 |
| F 02 | 370,000 | 4.66 | 2.18 | 12.30 | 46.5 | 2.5 | 17.5 |
| F 03 | 1,000,000 | 4.66 | 2.18 | 12.30 | 46.5 | 3.0 | 19.5 |
| F 04 | 1,000,000 | 3.76 | 2.18 | 12.30 | 46.5 | 3.0 | 19.0 |
| F 05 | 1,000,000 | 2.88 | 1.12 | 12.30 | 46.5 | 3.0 | 24.0 |
| F 08 | 100,000 | 8.95 | 1.57 | 11.43 | 46.5 | 3.0 | 20.0 |
| F 09 | 100,000 | 8.95 | 1.57 | 11.43 | 45.0 | 6.1 | 19.0 |
| F 10 | 100,000 | 8.95 | 2.10 | 11.87 | 60.0 | 2.0 | 24.0 |
| F 12 | 370,000 | 4.66 | 2.18 | 12.30 | 60.0 | 1.8 | 19.0 |
| F 13 | 370,000 | 4.66 | 2.18 | 12.30 | 70.0 | 1.9 | 20.0 |
| F 14 | 370,000 | 4.66 | 5.29 | 12.30 | 79.8 | 1.3 | 23.0 |
| F 15 | 370,000 | 4.66 | 2.18 | 12.30 | 60.0 | 21.2 | 17.0 |
| F 16 | 370,000 | 4.71 | 1.11 | 12.30 | 60.0 | 21.2 | 23.0 |
| F 17 | 370,000 | 4.66 | 2.18 | 12.30 | 60.0 | 10.7 | 23.0 |
| F 19 | 1,000,000 | 3.80 | 1.11 | 12.30 | 46.5 | 40.4 | 23.0 |
| F 20 | 370,000 | 3.80 | 1.12 | 12.30 | 46.5 | 40.4 | 23.0 |
| F 21 | 370,000 | 2.88 | 1.12 | 12.30 | 46.5 | 40.4 | 19.5 |
| F 22 | 370,000 | 1.94 | 1.12 | 12.30 | 46.5 | 40.4 | 21.0 |
| F 23 | 100,000 | 3.80 | 2.20 | 12.30 | 46.5 | 40.4 | 20.0 |
| F 27 | 370,000 | 2.90 | 0.28 | 12.30 | 46.5 | 40.4 | 22.5 |
| F 28 | 370,000 | 2.90 | 0.56 | 12.30 | 46.5 | 40.4 | 22.0 |
| F 41 | 100,000 | 8.95 | 1.57 | 12.30 | 40.0 | 2.0 | 23.0 |
| F 42 | 100,000 | 8.95 | 1.57 | 12.30 | 46.5 | 2.0 | 25.0 |
| F 43 | 370,000 | 5.60 | 1.09 | 12.30 | 42.0 | 5.7 | 24.0 |
| F 44 | 370,000 | 5.60 | 1.09 | 12.30 | 40.0 | 6.0 | 24.0 |
| F 45 | 370,000 | 5.60 | 1.09 | 12.30 | 46.5 | 5.5 | 24.0 |
| F 46 | 370,000 | 4.66 | 2.18 | 11.43 | 46.5 | 2.4 | 24.0 |
| F 47 | 370,000 | 4.66 | 2.18 | 11.43 | 46.5 | 10.7 | 24.0 |
| F48 | 100,000 | 4.66 | 2.18 | 11.43 | 46.5 | 10.7 | 100.00 |
| P18 | 100,000 | 12.66 | 2.98 | 12.30 | 46.5 | 1.8 | 23.5 |
| P17–S1 | 100,000 | 12.66 | 2.98 | 12.30 | 46.5 | 1.8 | 0.33 |

TABLE 2

| Sample Number | Porosity | Sorption Capacity of Foam (never dried) (g wet/g dry) | Sorption Capacity of Foam (after drying) (g wet/g dry) |
|---|---|---|---|
| F 01 | — | — | — |
| F 02 | 0.86 | 18 | 17 |
| F 03 | 0.81 | 16 | — |
| F 04 | 0.84 | 18 | 20 |
| F 05 | 0.86 | — | 27 |
| F 08 | 0.75 | 13 | 14 |
| F 09 | 0.69 | 10 | 10 |
| F 10 | 0.78 | 12 | 12 |
| F 12 | 0.87 | 24 | 25 |
| F 13 | 0.85 | 25 | 26 |
| F 14 | 0.82 | 19 | 20 |
| F 15 | 0.79 | 18 | 18 |
| F 16 | 0.79 | 18 | 20 |
| F 17 | 0.85 | 18 | 19 |
| F 19 | * | 18 | * |
| F 20 | 0.72 | 23 | — |
| F 21 | 0.87 | 34 | 22 |
| F 22 | 0.91 | 42 | 44 |
| F 23 | 0.86 | 25 | 24 |
| F 27 | * | * | * |
| F 28 | 0.91 | 36 | 33 |
| F 41 | 0.70 | 13 | 13 |
| F 42 | 0.81 | 11 | 12 |
| F 43 | 0.81 | 18 | 19 |
| F 44 | 0.77 | 21 | 21 |
| F 45 | 0.85 | 18 | 19 |
| F 46 | 0.81 | 20 | 21 |
| F 47 | 0.80 | 22 | 22 |
| F48 | 0.76 | 13 | 14 |
| P18 | 0.58 | — | 6.2 |
| P17-S1 | — | — | 6.5 |

EXAMPLE 3

Pore sizes were measured by conventional scanning electron microscopy (SEM), and the samples examined by this method were dried using the solvent-exchange method. Pore sizes were estimated from the size of the dark, roughly circular regions in the SEM micrographs, while pore struts were estimated from the size of the light, roughly linear areas. The results of SEM analysis are shown in Table 3 below. Applicants found that some of the foam samples tended to collapse to varying degrees upon conventional drying, however these foams would nevertheless fully swell when rehydrated. Applicants further found, however, that pore collapse could often be prevented by using a freeze-drying technique. The freeze-drying technique merely ensured a fully-expanded pore structure would exist for the SEM measurements, as virtually no structural collapse occurs. Additionally, freeze-drying does not significantly alter the equilibrium sorption properties of the foam. The foam samples were plunged into a dry-ice/ethanol slush until frozen. The samples were then transferred to a glass container and lyophilized at a pressure of less than 1 mmHg at −15° C. for at least 15 hours.

TABLE 3

| Sample Number | Pore Size ($\mu$m) | Strut Size ($\mu$m) |
|---|---|---|
| F 01 | 0.5–20 | 0.5–1.0 |
| F 02 | 0.2–2.5 | 0.2–0.6 |
| F 03 | 0.1–0.3 | — |
| F 04 | 0.1–0.5 | 0.1–0.3 |
| F 05 | 0.1–0.7 | 0.1–0.5 |
| F 08 | 1.0–15 | 1.5–2.5 |
| F 09 | 10–100 & 3–5 | 25–100 & 1.5–5 |
| F 10 | 0.6–6.0 | 0.5–2.0 |
| F 12 | 0.3–2.0 | 0.1–0.6 |
| F 13 | 0.3–3.0 | 0.1–0.6 |
| F 14 | — | — |
| F 15 | closed pores | closed pores |
| F 16 | 0.1–0.5 | 0.1–0.3 |
| F 17 | 0.1–0.5 | 0.1–1.0 |
| F19 | closed pores | closed pores |
| F20 | closed pores | closed pores |
| F21 | 0.1–0.5 | 0.07–0.15 |
| F 22 | 0.1–0.8 | 0.1–0.2 |
| F 23 | 0.06–0.4 | 0.06–0.3 |
| F 27 | 0.2–2.0 | 0.2–0.4 |
| F 28 | 0.2–1.5 | 0.1–0.3 |
| F 41 | 0.5–17 | 1.0–3.0 |
| F 42 | 0.5–9.0 | 0.5–2.5 |
| F 43 | 0.1–2.0 | 0.1–0.2 |
| F 44 | 0.1–2.0 | 0.2–0.6 |
| F 45 | 0.2–1.5 | 0.1–0.5 |
| F 46 | 0.2–4.0 | 0.3–1.0 |
| F 47 | 0.2–5.0 | 0.3–1.0 |
| F 48 | 15–50 & 2–5 | 15–50 & 2–7 |
| P18 | 0.5–5 | 1–2 |
| P17-S1 | 0.4–7 | — |

Most of the foam samples exhibited randomly interconnected polymer-dense regions (struts) with interconnected void spaces between them (pores). There were no distinct windows between the pores, and thus the foams were of the desired, "open-cell" variety. The molecular weight of the polymer greatly affects the pore size, as the pore size decreases drastically as the polymer molecular weight increases. This is likely due to the increased viscosity of the solutions as the molecular weight increases, which in turn reduces the phase separation rate. While some of the samples exhibited closed pores, a few of these were able to still function as superabsorbent foams (such as sample F15). This problem, however, can be eliminated merely by a minor change in the synthesis parameters for the foam, and could readily be accomplished by one skilled in the art.

EXAMPLE 4

In order to measure the ability of the foams to retain fluid under an applied pressure, creep tests were performed. Water-swollen foams were placed between two thin wire mesh screens, and this sandwich was then placed between flat plates connected to a strain gauge. A pressure of 0.75 psi (1.0 psi for some samples) was then applied to the sample until the thickness of the foam no longer decreased. The weight of the compressed foam was then compared to the weight of the swollen foam before application of the load in order to determine the percent of water retained by the foam under an applied pressure. Creep test measurements are shown in Table 4.

TABLE 4

| Sample Number | Percent Retention of Free-Swelling Capacity @ 0.75 psi (w/w %) | Sample Number | Percent Retention of Free-Swelling Capacity @ 0.75 psi (w/w %) |
|---|---|---|---|
| F 01 | — | F 20 | 53 |
| F 02 | 61 (@ 1.0 psi) | F 21 | 36 |
| F 03 | 61 (@ 1.0 psi) | F 22 | 25 |
| F 04 | 53 (@ 1.0 psi) | F 23 | 50 |
| F 05 | — | F 27 | 36 |
| F 08 | 79 | F 28 | 43 |
| F 09 | 95 | F 41 | 85 |
| F 10 | 94 | F 42 | 96 |
| F 12 | 63 | F 43 | 77 |
| F 13 | 62 | F 44 | 72 |
| F 14 | 62 | F 45 | 80 |
| F 15 | 77 | F 46 | 66 |
| F 16 | 66 | F 47 | 65 |
| F 17 | 72 | F 48 | 80 |
| F 19 | — | | |

As shown above, the foams produced by the method of the present invention exhibited excellent water retention under a considerable pressure. In fact, some of the foams retained over 90% of their absorbed water under a pressure of 0.75 psi. This is significant in that fluid retention under this magnitude of pressure is a highly-desirable property in applications such as diapers.

EXAMPLE 5

Direct wicking height measurements of the foam are impractical because such tests would require rather long strips of foam (10–50 cm), and thus an alternate method described in *Absorbency*, (edited by P. K. Chatterjee (Elsevier, 1985)) was employed. In this approach, the dry foam is contacted with a liquid such that absorption occurs under varying negative hydrostatic pressure. In order to ensure that an intact microstructure was maintained for all of the samples, however, a modified solvent-exchange drying technique was employed for the samples used in the wicking tests. Water was first expelled from the newly-synthesized foam by pressing the foam between absorbent tissues. The foam was then immersed in acetone for at least 20 minutes, thus stripping the pore walls of any remaining water. The acetone-swollen foam was then immersed in heptane for at least 40 minutes. While the heptane removed the acetone from the cell walls, it did not itself swell the pore walls because heptane is a non-solvent for HPC. The heptane was then readily removed from the pores by air-drying the foam for 10–20 minutes.

The wicking experiments were performed using a fritted glass filter plate placed in a funnel. The bottom of the funnel was connected to one end of a vertical, water-filled tube, and the other end of the tube was placed in a water reservoir. The length of the tube was either 10 cm or 30 cm, and the microporous glass frit had sufficient capillary pressure to support the column of liquid in the tube. The dry foam was then placed on the fitted glass plate where it was able to absorb water. The tube in this apparatus essentially acts as a substitute for a corresponding length of saturated foam through which the water would have wicked. The wicking ability of the foam was measured as the ratio of the weight of the water-swollen foam to the weight of the dry foam. The wicking test results are shown in Table 5.

TABLE 5

| Sample Number | Sorption Capacity of Foam @ 30 cm H$_2$O (.43 psi) (g wet/g dry) | Sorption Capacity of Foam @ 10 cm H$_2$O (.14 psi) (g wet/ g dry) |
| --- | --- | --- |
| F 01 | 5 | 6 |
| F 02 | 12 | 15 |
| F 03 | 9 | 12 |
| F 04 | 9 | 12 |
| F 05 | 8 | 10 |
| F 08 | 7 | 10 |
| F 09 | 8 | 9 |
| F 10 | 11 | 11 |
| F 12 | 8 | 13 |
| F 13 | 7 | 11 |
| F 14 | 9 | 13 |
| F 15 | 13 | 17 |
| F 16 | 12 | 17 |
| F 17 | 11 | 15 |
| F 19 | — | — |
| F 20 | — | — |
| F 21 | 8 | 14 |
| F 22 | 7 | 9 |
| F 23 | 11 | 21 |
| F 27 | 7 | 10 |
| F 28 | 7 | 10 |
| F 41 | 9 | 12 |
| F 42 | 10 | 11 |
| F 43 | 12 | 16 |
| F 44 | 10 | 18 |
| F 45 | 11 | 16 |
| F 46 | 9 | 14 |
| F 47 | 7 | 10 |
| F 48 | — | — |

While the wicking height (i.e., the height of water supported) is less than expected based upon the pore sizes measured by SEM, the results do indicate that the foams will retain fluid under a modest negative hydrostatic pressure. The results in Table 5 would also tend to indicate that the pores are not actually draining, but rather are collapsing while remaining water-filled. In other words, a portion of the fluid held by capillary action is released, while that held within the pore walls is retained. In this fashion, the behavior of the foams synthesized by the methods of the present invention lies between that typically exhibited by non-porous gels and that exhibited by conventional, porous solids. Further wick testing at varying water heights indicated that fluid retention remained relatively constant at heights greater than 30 cm H$_2$O, and a significant amount of fluid was retained by most of the foams at wicking heights as great as 60 cm H$_2$O.

EXAMPLE 6

The rate of sorption of the various foams was determined by placing a flat, dry foam sample on the surface of a dish of water. The foam samples used in this test were dried using the solvent-exchange method of Example 5. The time for the sample to completely swell was recorded, and the sample was then removed and weighed. The completeness of the swelling process was measured by either returning the sample to the dish of water for additional time and thereafter remeasuring the sample weight, or by comparing the measured weight with that obtained for a fully-swollen sample. The sorption rates are shown in Table 6, and vary from about 2 seconds to over half an hour. All of these sorption rates, however, are significantly shorter than prior art superabsorbents produced as sheets of a comparable size from the identical polymer.

TABLE 6

| Sample Number | Sorption Time (sec) | Sample Number | Sorption Time (sec) |
| --- | --- | --- | --- |
| F 01 | 9 | F 20 | — |
| F 02 | 4 | F 21 | >900 |
| F 03 | 240 | F 22 | >1320 |
| F 04 | 20 | F 23 | 2000 |
| F 05 | 95 | F 27 | 210 |
| F 08 | 9 | F 28 | 420 |
| F 09 | 6 | F 41 | 5 |
| F 10 | 5 | F 42 | 3 |
| F 12 | 5 | F 43 | 10 |
| F 13 | 15 | F 44 | 25 |
| F 14 | 4 | F 45 | 8 |
| F 15 | 300 | F 46 | 5 |
| F 16 | 90 | F 47 | 28 |
| F 17 | 5 | F 48 | 2 |
| F 19 | — | | |

EXAMPLE 7

In order to examine the effect of the drying method on the foam properties, three foam samples of relatively high sorption capacity (F12, F13 and F17) were dried by the three methods described previously (air-drying, solvent-exchange, and freeze-drying). The water-swollen foam samples which were air-dried were first pressed between layers of absorbent material to remove water present in the pores. The foams were then air dried (@ 26° C.) completely in 2–3 hours. These air dried samples appeared either transparent or translucent (as opposed to milky white) with little or no air-filled pores present. It was thus apparent that this drying technique caused the pores present in the foam to collapse (to a non-porous state, rather than a porous state). Even the air-dried samples absorbed a considerable amount of water, however, and the sorption capacity of the foam was not significantly affected by the manner of drying. The rate of sorption was affected, however, and the results are shown below in Table 7.

TABLE 7

| Sample Type | Air-Dried (sec) | Solvent-Exchange (sec) | Freeze-Dried (sec) |
| --- | --- | --- | --- |
| F 12 | 45 | 5 | 2100 |
| F 13 | 60 | 15 | 3300 |
| F 17 | 38 | 5 | 300 |

While the sorption times for the air-dried samples were significantly greater than those dried by the solvent-exchange method, they were still less than a minute. Although the freeze-dried samples took considerably longer to swell, however, most of the absorption in the freeze-dried samples took place rather quickly (at a rate comparable to the other samples). Thus, freeze-dried samples F12, F13 and F17 absorbed 20, 15, and 17 times their dry weights in only 30, 35 and 12 seconds, respectively. While the reason for this anomaly is unclear, it is believed that freeze-drying may have "over-dried" the foam, thereby removing molecularly bound water from the polymer and enhancing polymer-polymer attraction in the dry state.

EXAMPLE 8

Since commercially available HPC has a relatively high degree of substitution (>2.5), and therefore does not readily biodegrade, foams were produced from high viscosity hydroxyethyl cellulose (HEC) (Aldrich Chemical Co.) using the same techniques described previously. Commercially-available HEC has a lower degree of substitution (0.9–1.0), and therefore the resultant foams would be expected to biodegrade more quickly than a foam made from HPC.

While an aqueous HEC solution does not exhibit an LCST, and therefore does not phase separate upon heating, it is known that the addition of a solute such as a salt can lower the LCST of an aqueous polymer solution. Applicants found that by saturating an aqueous solution of HEC with sodium chloride (about 24 wt % salt), the solution exhibited an LCST of less than 95° C. Thus, when the temperature of such a salt-saturated polymer solution was increased to at least about 95° C., the solution phase-separated, and thus was amenable to the method of the present invention.

Table 8 below provides the synthesis parameters for HEC foams produced by the method of the present invention. It should be noted that if sufficient amounts of crosslinker were not present, a sufficient interconnected structure would not be formed. For example, a crosslinker level significantly below about 0.40 wt. % did not produce a foam with the synthesis parameters of samples F61 and F62. The procedures employed for the examples of Table 8 were identical to those previously described (synthesis at pH 12.3), however the sheets were repeatedly swelled in water to ensure a complete removal of the sol fraction and salt present in the foam. The sheets were then dried using the solvent-exchange method described previously in order to ensure that the foam structure did not collapse. The solvents preferably employed for HEC foam drying are ethanol, followed by pentane, however numerous other solvents could be employed.

properties than comparable HPC foams. It should be noted that sample F96 was permitted to crosslink for too long a period of time, and the high temperature and pH caused the foam to degrade into a polymer solution. One skilled in the art, however, can easily rectify this problem by reducing the reaction time during phase separation.

In addition, stress-strain measurements on the two foam types (using a Rheometrics RSA-II solid analyzer) revealed that the HEC foams were considerably stronger than comparable HPC foams. This is likely due to more efficient crosslinking of HEC. More importantly, however, this testing demonstrated that the principles of foam synthesis garnered from the production of HPC foams can be generalized to other polymer/solvent systems, wherein the solution can be induced to phase separate. In the case of HEC/water, the addition of sodium chloride produces the desired phase separation mechanism. The addition of other solutes or solvents will produce similar effects on phase separation to varying degrees.

As expected, granulation of HEC foams also had a marked effect on the sorption rates, as these rates were even less than those given in Table 9. While the absorbance under load for the granulated foams were less than that for foam sheets, applicants believe that these results were due to inadvertent improper drying of the samples used for these tests.

Applicants have found that the superabsorbent foams produced by the methods of the present invention have a sorption rate which is at least 100 times faster that a conventionally-made, non-porous superabsorbent sheet of comparable size made, even wherein the non-porous superabsorbent is made from the very same polymer as the foam.

TABLE 8

| Sample Number | Initial Polymer Conc. wt % | Initial Conc. wt % | Na Cl Conc. wt % | Phase Separation Temp °C. | Rxn. Time before Phase Separation (sec) | Rxn. Time During Separation (hours) |
| --- | --- | --- | --- | --- | --- | --- |
| F 61 | 6.87 | 0.40 | 24.0 | 98.7 | 240 | 7.5 |
| F 62 | 6.87 | 0.40 | 24.0 | 98.7 | 195 | 6.5 |
| F 53 | 3.46 | 1.62 | 25.6 | 94.9 | 156 | 1.0 |
| F 98 | 3.51 | 1.64 | 25–27.7% | 95.7 | 126 | 0.32 |
| F 96 | 3.50 | 1.67 | 25–27.7% | 95.0 | 150 | 24 |
| F 97 | 2.83 | 1.67 | 25–27.7% | 95.0 | 156 | 1.03 |

In order to characterize the HEC foams, tests similar to those previously described for HPC foams were employed. The results of these tests are shown in Table 9. It should be noted that foam F52 was too weak to be properly characterized by the test methods employed.

TABLE 9

| Sample Number | Sorption Capacity g wet/ g dry | Percent Retention of Free Swelling Capacity (w/w%) (creep test) | Sorption Capacity @ 50 cm H2O g wet/ g dry (wicking test) | Sorption Time (sec) |
| --- | --- | --- | --- | --- |
| F 61 | 16 | — | — | — |
| F 53 | 17 | 88 (@ 0.75 psi) | 15 | 9 |
| F 98 | 18 | — | 15 | 8 |
| F 96 | no foam formed | — | — | — |
| F 97 | 26 | — | 14 | 12 |

From the results shown in Table 9, it is apparent that HEC foams generally have better fluid retention and wicking In addition, as noted above, conventional, non-porous superabsorbents (e.g., commercially-available, superabsorbent poly(sodium acrylate)) are usually granulated in order to improve their swelling capacity and sorption rate. These conventional superabsorbents, however, must also be mixed with a fluff material because of the gel blocking phenomenon. The fluff wicks the fluid to the non-porous, superabsorbent, where the fluid is absorbed. The use of this fluff, however, significantly increases the thickness of the absorbent layer of a product such as a diaper. Applicants have found that their microporous, superabsorbent foam sheets have at least the same swelling capacity, and a comparable sorption rate, as a conventionally-made, non-porous superabsorbent which has been ground and combined with fluff (even if Applicants' foam and the conventional superabsorbent are produced from the very same polymer). Applicants' foams are able to wick fluid into the interior of the foam without blocking the spaces between absorptive polymer regions, unlike the conventional, non-porous superabsorbents. Obviously, a thin, superabsorbent sheet, with no additional fluff, is particularly advantageous in products such as diapers and feminine hygiene devices. Sorption kinetics for conventional, non-porous, superabsorbents are available, for example, in *Kinetics of Swellin of Absorbent Polymers*, F. L. Buchholz. It should be pointed out that when the foams of the present invention are to be used for absorbing aqueous solutions (e.g., in diapers), it is essential that a hydrophilic polymer be employed in the synthesis. Applicants' foams also do not significantly lose their desired sorption properties (e.g., capacity and rate) even after repeated drying and resorption of fluid. In addition, Applicants' foams can be flattened in the dry state while still retaining the ability to absorb fluid and expand.

It will be understood that modifications may be made in the present invention without departing from the spirit of it. For example, various other types of polymers, solvents and crosslinkers other than those specifically disclosed may be effectively employed to practice the process of the present invention. Thus, the scope of the present invention should be considered in terms of the following claims, and is understood not to be limited to the details of structure and operation shown and described in the specification.

What we claim is:

1. A microporous, open-celled foam produced by the method comprising the steps of:

(a) mixing hydroxypropyl cellulose (HPC) and water to form a substantially homogeneous, single-phase solution;

(b) inducing crosslinking of said HPC by adding a suitable crosslinking agent to said single-phase solution;

(c) inducing phase separation of said single-phase solution into a polymer-concentrated phase and a polymer-dilute phase wherein said phase separation is induced by increasing the temperature of said single-phase solution to above the lower consolute solution temperature of said single-phase solution;

(d) permitting said crosslinking to continue, so that said HPC will crosslink in said concentrated phase for a predetermined period of time during said phase separation to thereby form a microporous material; and (e) drying said microporous material to produce said microporous foam.

2. A microporous, open-celled foam produced by the method comprising the steps of:

(a) mixing hydroxyethyl cellulose (HEC), water and a phase-separation enhancer to form a substantially homogeneous, single-phase solution, wherein said phase-separation enhancer is chosen from the group consisting of salts, water-soluble organic solvents, and combinations of salts and water-soluble organic solvents;

(b) inducing crosslinking of said HEC by adding a suitable crosslinking agent to said single-phase solution;

(c) inducing phase separation of said single-phase solution into a polymer-concentrated phase and a polymer-dilute phase, wherein said phase separation is induced by increasing the temperature of said single-phase solution to above the lower consolute solution temperature of said single-phase solution;

(d) permitting said crosslinkin to continue, so that said HEC will crosslink in said concentrated phase for a predetermined period of time during said phase separation to thereby form a microporous material; and (e) drying said microporous material to produce said microporous foam.

3. An absorbent, microporous foam comprising a crosslinked polymer having interconnected fluid cells distributed throughout the mass of said foam, wherein said fluid cells have a diameter of between about 0.1 and about 100 $\mu$m, and wherein said foam can rapidly absorb at least about twice its dry weight in fluid, and wherein said crosslinked polymer is selected from the group consisting of hydroxypropyl cellulose (HPC); hydroxyethyl cellulose (HEC); and mixtures thereof.

4. The foam of claim 3, wherein said foam absorbs and retains fluid by a combination of capillary action and pore wall swelling.

5. The foam of claim 3, wherein said foam is superabsorbent, capable of absorbing at least about ten times its dry weight in fluid.

6. An absorbent microporous foam capable of absorbing at least ten times its dry weight in fluid comprising a cross-linked polymer having interconnected fluid cells distributed throughout the mass of said foam, wherein said fluid cells have a diameter of between about 0.1 and about 100 $\mu$m, and wherein said cross-linked polymer is selected from the group consisting of hydroxypropyl dextran; hydroxypropyl guar; hydropropyl starch; hydroxypropyl cellulose, hydroxyethyl cellulose; methyl cellulose; hydropropyl methyl cellulose; ethylhydroxyethyl cellulose; and mixtures thereof.

* * * * *